(12) United States Patent
Kwak et al.

(10) Patent No.: US 10,533,933 B2
(45) Date of Patent: *Jan. 14, 2020

(54) NUCLEAR MAGNETIC RESONANCE GAS ISOTHERM TECHNIQUE TO EVALUATE RESERVOIR ROCK WETTABILITY

(71) Applicant: Saudi Arabian Oil Company, Dhahran (SA)

(72) Inventors: Hyung Tae Kwak, Dhahran (SA); Ahmad Mubarak Al-Harbi, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 16/182,280

(22) Filed: Nov. 6, 2018

(65) Prior Publication Data
US 2019/0086312 A1 Mar. 21, 2019

Related U.S. Application Data

(63) Continuation-in-part of application No. 15/463,679, filed on Mar. 20, 2017, now Pat. No. 10,145,774, (Continued)

(51) Int. Cl.
*G01N 11/00* (2006.01)
*G01V 3/32* (2006.01)
(Continued)

(52) U.S. Cl.
CPC ........... *G01N 11/00* (2013.01); *G01N 24/081* (2013.01); *G01N 24/082* (2013.01);
(Continued)

(58) Field of Classification Search
CPC .......... G01N 11/00; G01N 2011/0006; G01N 2011/0086; G01N 24/081; G01R 33/305;
(Continued)

(56) References Cited

U.S. PATENT DOCUMENTS 5,433,717 A 7/1995 Rubinsky et al.
7,397,240 B2 7/2008 Fleury et al.
(Continued)

FOREIGN PATENT DOCUMENTS

JP 2008203154 9/2008

OTHER PUBLICATIONS

Chinese Office Action issued in Chinese Application No. 201680033764.8 dated May 5, 2019, 15 pages.
(Continued)

*Primary Examiner* — Rishi R Patel
(74) *Attorney, Agent, or Firm* — Fish & Richardson P.C.

(57) ABSTRACT

Nuclear magnetic resonance (NMR) gas isotherm techniques to evaluate wettability of porous media, such as hydrocarbon reservoir rock, can include constructing a NMR gas isotherm curve for a porous media sample gas adsorption under various pressures. A hydrophobic or hydrophilic nature of the porous media sample can be determined using the NMR gas isotherm curves. A wettability of the porous media sample can be determined based on the NMR gas isotherm curve. The wettability can be determined for porous media samples with different pore sizes. In the case of reservoir rock samples, the determined wettability can be used, among other things, to model the hydrocarbon reservoir that includes such rock samples, to simulate fluid flow through such reservoirs, or to model enhanced hydrocarbon recovery from such reservoirs.

20 Claims, 6 Drawing Sheets

Related U.S. Application Data which is a continuation of application No. 15/069,650, filed on Mar. 14, 2016, now Pat. No. 9,599,581.

(60) Provisional application No. 62/276,120, filed on Jan. 7, 2016, provisional application No. 62/151,079, filed on Apr. 22, 2015.

(51) Int. Cl.
*G01N 24/08* (2006.01)
*G01R 33/30* (2006.01)
*G01R 33/44* (2006.01)
*G01R 33/561* (2006.01)

(52) U.S. Cl.
CPC .......... *G01R 33/305* (2013.01); *G01R 33/448* (2013.01); *G01V 3/32* (2013.01); *G01N 2011/0006* (2013.01); *G01N 2011/0086* (2013.01); *G01R 33/5617* (2013.01)

(58) Field of Classification Search
CPC .. G01R 33/448; G01R 33/5617; G01R 33/44; G01R 33/445; G01V 3/32
See application file for complete search history.

(56) References Cited

U.S. PATENT DOCUMENTS

| | | | |
|---|---|---|---|
| 9,176,081 | B2 | 11/2015 | Sen et al. |
| 9,599,581 | B2 | 3/2017 | Kwak |
| 10,145,774 | B2 | 12/2018 | Kwak et al. |
| 2007/0241753 | A1 | 10/2007 | Sodickson |
| 2008/0303520 | A1 | 12/2008 | Chen |
| 2011/0201892 | A1 | 8/2011 | Haig et al. |
| 2013/0313267 | A1 | 11/2013 | Horio et al. |
| 2015/0219782 | A1 | 8/2015 | Viswanathan et al. |
| 2016/0290942 | A1 | 10/2016 | Wang et al. |
| 2019/0113429 | A1* | 4/2019 | Kwak .................... G01N 11/00 |

OTHER PUBLICATIONS

Gulf Cooperation Council Examination Report issued in GCC Application No. GC 2016-31196 dated Oct. 22, 2018, 3 pages.
Chinese Office Action issued in Chinese Application No. 201680033764.8 dated Nov. 26, 2018, 16 pages.
Abdallah et al., "Fundamentals of Wettability," Oilfield Review, Summer 2007, 18 pages.
Bortolotti et al, "Probing Wettability Reversal in Carbonatic Rocks by Spatially-Resolved and Non-Resolved 1H-NMR Relaxation Analysis," Proceedings—SPE Annual Technical Conference and Exhibition 2010, Society of Petroleum Engineers, vol. 2, SPE 133937, Sep. 19-22, 2010, pp. 1483-1491, 9 pages.
Bryar et al., "Laboratory Studies of the Effect of Sorbed Oil on Proton Nuclear Magnetic Resonance", Geophysics vol. 68, No. 3, May-Jun. 2003, pp. 942-948.
Fleury and Deflandre, "Quantitative evaluation of porous media wettability using NMR relaxometry," Magnetic Resonance Imaging vol. 21, Issue 3-4, Apr.-May 2003, 3 pages.
Freedman et al., "Wettability, Saturation, and Viscosity from NMR Measurements", Dec. 2003, 11 pages.
Gugliotti, "Tears of Wine," Journal of Chemical Education, vol. 81, No. 1, Jan. 2004, 2 pages.
Hitchcock et al, "NMR Studies of Cooperative Effects in Adsorption," Langmuir, American Chemical Society, vol. 26, No. 23, Dec. 7, 2010, pp. 18061-18070, 10 pages.
Kleinhammes et al., "Gas absorption in single-walled carbon nanotubes studied by NMR," Physical Review B, vol. 68, American Physical Society, Aug. 2003, 6 pages.
Knight et al., "The Use of Dielectric and NMR Measurements to Determine the Pore-Scale Location of Organic Contaminants", Jul. 15, 1997, 9 pages.
Korb et al., "Using multifrequency NMR for probing wettability," SCA2010-15, presented at the International Symposium of the Society of Core Analysts, Oct. 4-7, 2010, 12 pages.
Kwak et al., "Toward a Method for measuring wettability in porous media by NMR water vapor isotherm technique," presented at the International Symposium of the Society of Core Analysts held in Vienna, Austria, Aug. 27-Sep. 1, 2017, 9 pages.
Li et al, "Spin Echo SPI Methods for Quantitative Analysis of Fluids in Porous Media," Journal of Magnetic Resonance, vol. 198, No. 2, Academic Press: Orlando, FL, US, Jun. 1, 2009, pp. 252-260.
Looyestijn et al., "Wettability Index Determination by Nuclear Magnetic Resonance," SPE International Oil and Gas Conference and Exhibition, No. SPE9362, Mar. 12, 2005, 8 pages.
Lucas et al, "Quantitative Porosity Mapping of Reservoir Rock Cores by Physically Slice Selected NMR," Herchel Smith Laboratory for Medicinal Chemistry, 1993, pp. 3-24.
Mao et al., "NMR Studies of Gas and Water Adsorption in Carbon Based Materials", published in 2007, 134 pages.
Mao et al., "NMR study of water absorption in single-walled carbon nanotubes," Chemical Physics Letters 421, Issue 4-6, Apr. 15, 2006, 5 pages.
Oztop et al, "Using multi-slice-multi-echo images with NMR relaxometry to assess water and fat distribution in coated chicken nuggets," Food Science and Technology 55.2, Mar. 2014, pp. 690-694, 5 pages.
Peters, Ekwere J., "Advanced Petrophysics: Geology, porosity, absolute permeability, heterogeneity, and geostatistics," vol. 1, Greenleaf Book Group, 2012, pp. 50-53.
Petrov et al., "$T_2$ distribution mapping profiles with phase-encode MRI", vol. 209, Mar. 2011, pp. 39-46, 9 pages.
Tipura, "Wettability Characterization by NMR T2 Measurements in Edwards Limestone", Master Thesis in Reservoir Physics, Universitas Bergensis, published in Mar. 2008, 91 pages.
Wang et al., "Temperature-Induced Hydrophobic-Hydrophilic Transition Observed by Water adsorption," Science, vol. 322, Issue 5898, Oct. 2008, 4 pages.
Wang et al., "Water Adsorption in Nanoporous Carbon Characterized by in Situ NMR: Measurements of Pore Size and Pore Size Distribution," The Journal of Physical Chemistry C, American Chemical Society Publications, Apr. 2014, 7 pages.
Wasiuddin et al., "Effect of Sasobit and Aspha-Min on Wettability and Adhesion Between Asphalt Binders and Aggregates," Transportation Research Record: Journal of the Transportation Research Board, No. 2051, Dec. 2008, 10 pages.
Zhang et al., "Interpretations of Wettability in Sandstones with NMR Analysis", SCA-9921, May 2000, 13 pages.
International Search Report and Written Opinion issued in International Application No. PCT/US2016/027239, dated Jul. 14, 2016, 14 pages.

\* cited by examiner

NUCLEAR MAGNETIC RESONANCE GAS ISOTHERM TECHNIQUE TO EVALUATE RESERVOIR ROCK WETTABILITY

CROSS-REFERENCE TO RELATED APPLICATIONS

This application is a Continuation in Part of and claims the benefit of priority under 35 USC § 120 to U.S. patent application Ser. No. 15/463,679, filed on Mar. 20, 2017, which is a continuation of U.S. patent application Ser. No. 15/069,650, filed on Mar. 14, 2016, now Issued as U.S. Pat. No. 9,599,581, issued on Mar. 21, 2017, which claims the benefit of priority under 35 USC § 119(e) to U.S. Provisional Application Ser. No. 62/151,079, filed on Apr. 22, 2015 and U.S. Provisional Application Ser. No. 62/276,120, filed on Jan. 7, 2016, the contents of each and all of which are hereby incorporated by reference in its respective entirety.

TECHNICAL FIELD

This specification relates to exploration and production of hydrocarbons, and, more specifically, to detecting reservoir properties.

BACKGROUND

Rocks in a hydrocarbon reservoir store hydrocarbons (for example, petroleum, oil, gas, or combinations of one or more of them), for example, by trapping the hydrocarbons within porous formations in the rocks. Understanding properties of the hydrocarbon reservoir can assist to optimize extraction of the stored hydrocarbons from the reservoir. One technique to understand properties of the hydrocarbon reservoir is to develop computer-generated software models of all or portions of the reservoir. To develop such models, a reservoir rock sample from the hydrocarbon reservoir is evaluated and results of the evaluation are provided as an input to the computer software program that generates the software models. The reservoir rock sample can be evaluated by performing one or more of several experiments under laboratory conditions or under reservoir conditions (that is, the conditions experienced by the sample in the hydrocarbon reservoir). Rock wettability, specifically, the wettability of the porous structure within the rock, is one of the parameters of the reservoir rock sample that can be evaluated.

SUMMARY

This specification describes technologies relating to nuclear magnetic resonance (NMR) gas isotherm technique to evaluate reservoir rock wettability.

Certain aspects of the subject matter described here can be implemented as a method. Multiple pressures are applied to a three-dimensional reservoir rock sample in a closed volume. The reservoir rock sample includes multiple porous regions distributed along a longitudinal axis of the reservoir rock sample. The multiple porous regions have a respective multiple of wettabilities. Each wettability represents a quality of each porous region to absorb gas. At each pressure of the multiple pressure, a spin-echo single-point imaging (SE-SPI) pulse sequence is applied to the multiple porous regions distributed along the longitudinal axis of the reservoir rock sample. A nuclear magnetic resonance (NMR) gas isotherm curve is constructed for the reservoir rock sample in response to applying the multiple pressures. At each pressure of the multiple pressures, the SE-SPI pulse sequence is applied to the multiple porous regions distributed along the longitudinal axis of the reservoir rock sample. The multiple wettabilities are determined for the multiple porous regions based on the NMR gas isotherm curve. Each wettability of the multiple wettabilities includes a value representing the quality of each porous region to absorb gas. A spatial wettability distribution for the reservoir rock sample is determined based on the multiple wettabilities. The spatial wettability distribution for the reservoir rock sample is provided.

This, and other aspects, can include one or more of the following features. The NMR gas adsorption isotherm curve can include an NMR hydrogen gas adsorption isotherm curve, and the rock sample can be saturated with water to a desired water saturation level. It can be determined that the NMR gas isotherm curve is a convex curve. It can be determined that the reservoir rock sample includes more hydrophilic surfaces than hydrophobic surfaces in response to determining that the NMR gas isotherm curve is a convex curve. It can be determined that the NMR gas isotherm curve is a concave curve. It can be determined that the reservoir rock sample includes more hydrophobic surfaces than hydrophilic surfaces in response to determining that the NMR gas isotherm curve is a concave curve. The spatial wettability of the reservoir rock sample can be determined based on whether the reservoir rock sample includes more hydrophilic surfaces or more hydrophobic surfaces. A porosity of the multiple porous regions can range between less than a micrometer and greater than a micrometer. To determine the spatial wettability of the rock sample, a first wettability of a first porous region of the reservoir rock sample having a porosity less than a micrometer can be determined, a second wettability of a second porous region of the reservoir rock sample having a porosity greater than or equal to a micrometer can be determined. To determine the multiple wettabilities for the multiple porous regions based on the NMR gas isotherm curve, the NMR gas isotherm curve for the reservoir rock sample gas adsorption can be compared with a first standard NMR gas isotherm curve for a hydrophobic sample and a second standard NMR gas isotherm curve for a hydrophilic sample. A NMR gas isotherm curve can be constructed for the hydrophobic sample. A NMR gas isotherm curve can be constructed for the hydrophilic sample. The hydrophobic sample includes beads coated with a hydrophobic coating. The hydrophilic sample includes beads coated with a hydrophilic coating. To determine the multiple wettabilities for the multiple porous regions based on the NMR gas isotherm curve, a first quantitative value for a first porous region having a porosity ranging less than a micrometer and a second quantitative value for a second porous region having a porosity ranging greater than or equal to a micrometer can be determined. To determine the first quantitative value, a normalized area under the NMR gas isotherm curve can be determined for the first porous region. To determine the first value, it can be determined that the reservoir rock sample is oil wet in response to determining that the normalized area under the curve is between 0 and substantially 0.5, that the reservoir rock sample is intermediate wet in response to determining that the normalized area under the curve is substantially equal to 0.5, or that the reservoir rock sample is water wet in response to determining that the normalized area under the curve is between substantially 0.5 and 1. To determine the second value, a ratio of a difference between a gas adsorption amount of the reservoir rock sample and a gas adsorption amount of the hydrophobic sample and a difference between a gas adsorption amount of the hydrophilic sample and the gas adsorption amount of the hydrophobic sample can be determined. To determine the second quantitative value, it can be determined that the reservoir rock sample is oil wet in response to determining that the ratio is between 0 and substantially 0.5, that the reservoir rock sample is intermediate wet in response to determining that the ratio is substantially equal to 0.5 or that the reservoir rock sample is water wet in response to determining that the ratio is between substantially 0.5 and 1. To determine the second quantitative value, a ratio between a gas adsorption of the reservoir rock sample and a gas adsorption of the hydrophilic sample can be determined. To apply a SE-SPI pulse sequence at each pressure of the multiple pressures, while applying each pressure, the SE-SPI pulse sequence can be applied to the multiple porous regions in the reservoir rock sample, and, for each porous region, a T2 decay time responsive to the applied pressure can be measured.

Certain aspects of the subject matter described here can be implemented as a system. The system includes a nuclear magnetic resonance (NMR) sample call configured to receive a reservoir rock sample including multiple porous regions distributed along a longitudinal axis of the reservoir rock sample. The multiple porous regions have respective multiple wettabilities. Each wettability represents a quality of each porous region to absorb gas. The system includes a pressure delivery system connected to the NMR sample cell. The pressure delivery system is configured to apply multiple pressures to the reservoir rock sample in the NMR sample cell. The system includes a NMR control system connected to the NMR sample cell. The NMR control system is configured to, at each pressure of the multiple pressures, apply a spin-echo single-point imaging (SE-SPI) pulse sequence to the multiple porous regions distributed along the longitudinal axis of the reservoir rock sample. The system includes a computer system connected to the NMR control system and the pressure delivery system. The computer system includes a computer-readable medium storing instructions executable by the computer system to perform operations. The operations include constructing a NMR gas isotherm curve for the reservoir rock sample in response to applying the multiple pressures and, at each pressure, applying the SE-SPI pulse sequence to the multiple porous regions. The operations include determining the multiple wettabilities for the multiple porous regions based on the NMR gas isotherm curve, each wettability including a value representing the quality of each porous region to absorb gas. The operations include determining a spatial wettability distribution for the reservoir rock sample based on the multiple wettabilities and providing the spatial wettability distribution for the reservoir rock sample.

This, and other aspects, can include one or more of the following features. The pressure delivery system can be configured to apply the multiple pressures using hydrocarbon gas. The NMR gas adsorption isotherm curve includes an NMR hydrocarbon gas adsorption isotherm curve. The rock sample can be saturated with water to a desired water saturation level. The operations to determine the multiple wettabilities include determining a first quantitative value for a first porous region having a porosity ranging less than a micrometer. The operations to determine the first quantitative value include determining that the reservoir rock sample is oil wet in response to determining that the normalized area under the curve is between 0 and substantially 0.5, that the reservoir rock sample is intermediate wet in response to determining that the normalized area under the curve is substantially equal to 0.5, or that the reservoir rock sample is water wet in response to determining that the normalized area under the curve is between substantially 0.5 and 1. The operations to determine the multiple wettabilities for the multiple porous regions includes determining a second quantitative value for a second porous region having a porosity ranging greater than or equal to a micrometer. The operations include determining that the reservoir rock sample is oil wet in response to determining that the ratio is between 0 and substantially 0.5, that the reservoir rock sample is intermediate wet in response to determining that the ratio is substantially equal to 0.5, or that the reservoir rock sample is water wet in response to determining that the ratio is between substantially 0.5 and 1.

Certain aspects of the subject matter described here can be implemented as a method. Multiple pressures are applied to a three-dimensional reservoir rock sample in a closed volume. The reservoir rock sample includes multiple porous regions distributed along a longitudinal axis of the reservoir rock sample. The multiple porous regions have respective multiple wettabilities. Each wettability represents a quality of each porous region to absorb gas. At each pressure, a NMR pulse sequence is applied to the multiple porous regions distributed along the longitudinal axis of the reservoir rock sample. A NMR gas isotherm curve is constructed for the rock sample in response to applying the multiple pressures and, at each pressure, applying the NMR pulse sequence. The multiple wettabilities for the multiple porous regions are determined based on the NMR gas isotherm curve. Each wettability includes a value representing the quality of each porous region to absorb gas. A spatial wettability distribution for the reservoir rock sample is determined based on the multiple wettabilities. The spatial wettability distribution is provided for the reservoir rock sample.

This, and other aspects, can include one or more of the following features. The NMR pulse sequence is either a Carr-Purcell-Meiboom-Gill (CPMG) pulse sequence or a Spin Echo Single Point Imaging (SE-SPI) pulse sequence To construct the NMR gas isotherm for the reservoir rock sample in response to applying the NMR pulse sequence to the multiple porous regions distributed along the longitudinal axis of the reservoir rock sample, while applying each pressure, the NMR pulse sequence can be applied to the multiple porous regions in the reservoir rock sample, and, for each porous region, a T2 decay time responsive to the applied pressure can be measured.

The details of one or more implementations of the subject matter described in this specification are set forth in the accompanying drawings and the description that follows. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
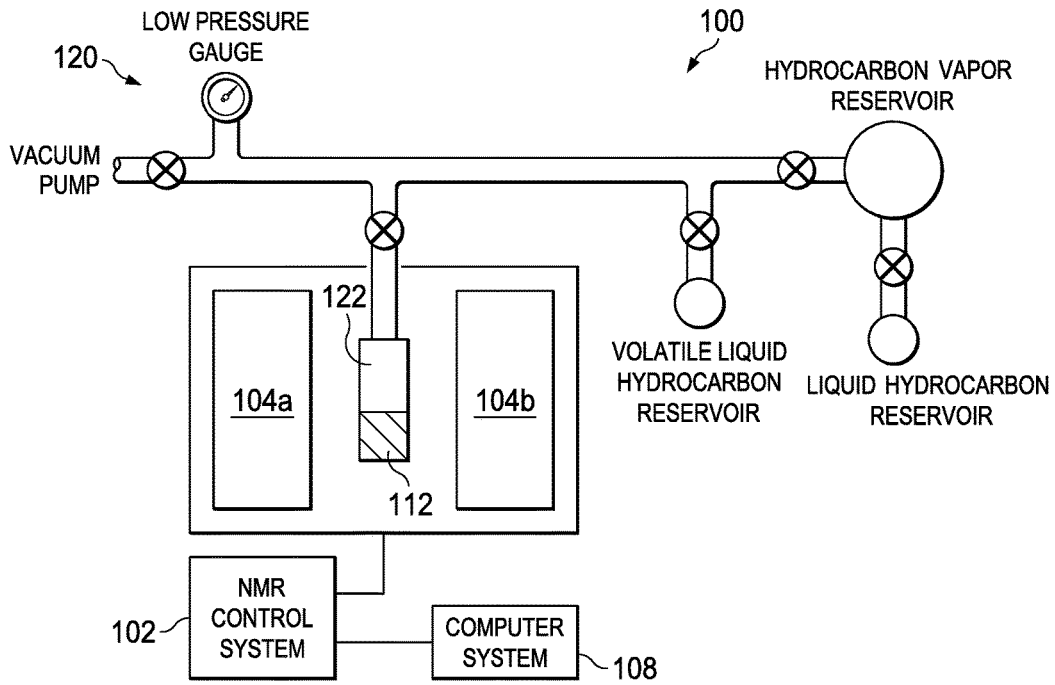
FIG. 1 is a schematic diagram of a system for determining a wettability of a sample of a reservoir rock sample using the NMR gas isotherm technique.

Rock wettability, specifically, the wettability of the porous structure within rocks, is one of the parameters that affect fluid flow through rocks. Rock wettability, therefore, is an input variable for geophysical models that predict flow through reservoir rocks. Wettability is often used as a distinguishing characteristic of reservoir rocks, designating the rocks as either hydrophobic or hydrophilic. Wettability is a material parameter characteristic of a given rock, for example, sandstone, carbonate or other rock, and additionally depends on factors such as surface roughness, surface size, existence of primary adsorption sites, specific ion effect and other additional factors. One technique to determine wettability of a surface (that is, the ability of the surface to retain moisture) is to add a drop of water to an idealized surface and to measure the contact angle of the water on the surface. The determined wettability can be provided as an input variable to geophysical model (a computer-generated or otherwise). The input variable will be more accurate and the predictions of the geophysical models will be truer if the wettability were determined for a porous structure of actual rocks, for example, under conditions that resemble and mimic rock environments.

Macroscopic experiments to determine wettability (for example, contact angle determination experiments) may have limited value to determine wettability within the porous structure of a reservoir rock sample. Some wettability measurement methods (for example, United States Bureau of Mines (USBM) test or Amott-Harvey test) are indirect methods with multiple experimental procedures which increase the likelihood of errors in the test results. In addition, both the USBM and Amott-Harvey tests, which measure the wettability of the interior pore surfaces, cannot be performed under known reservoir conditions.

This specification describes nuclear magnetic resonance (NMR) gas isotherm technique to evaluate rock wettability. The techniques described in this specification can be implemented to measure global and spatial wettability of a porous structure within a reservoir rock sample. It has been shown that NMR gas adsorption isotherm curve shape on the surface of a single-walled carbon nanotube with different surface gas affinity varies from hydrophobic to hydrophilic. This discovery shows a direct relationship between wettability and hydrophobicity of a solid surface. Implementing NMR gas isotherm to evaluate the wettability of a reservoir rock sample can provide an accurate wettability for pores with different sizes including sub-micrometer sized pores since gas can easily enter such pores. Further, as described later, the NMR gas isotherm technique can be combined with relaxation time (T2) mapping techniques by Spin-Echo Single Point Imaging (SE-SPI) pulse sequence to provide spatial wettability of the interior pore surface of any porous material including, for example, a sample of a reservoir rock. A comparison of certain known wettability measurement techniques with the NMR gas isotherm technique described in this disclosure are shown in the table below.

| Technique | Quantitative | Measurement Time | Multiple Experiments | Under Reservoir Conditions | Wettability of interior of porous media |
|---|---|---|---|---|---|
| Ammott-Harvey | Yes, but questionable | 10-12 days | Yes | Yes | Yes |
| USBM | Yes, but questionable | 1-2 days | Yes | Yes | Yes |
| Contact Angle | No | 1-2 hrs | No | Yes | No |
| NMR technique | Yes | 1-3 hrs | No | Yes | Yes |

$^1$H NMR signal intensity is proportional to the number of $^1$H inside a detected sample volume. By monitoring the total amount of surface adsorbed $^1$H of gas peak changes as the confining pressure changes, NMR gas isotherm curve can be constructed. The wettability measurement based on NMR gas isotherm is a direct measurement which can be conducted under reservoir condition without destroying the sample. The specific characteristics of the isotherm, such as shape and end point, are a function of relative vapor pressure for hydrophilic and hydrophobic surfaces. For sub-micrometer sized pores, hydrophilic surfaces produce a convex isotherm while hydrophobic surfaces produce a concave isotherm. For pores greater than or equal to a micrometer in size, the total amount of adsorbed gas is greater for pores with hydrophilic surfaces compared to those with hydrophobic surfaces. Thus, the shape or the end point (or both) of an isotherm obtained from a reservoir rock sample can enable the determination of whether the sample includes hydrophilic or hydrophobic surfaces. In addition to the isotherms, $^1$H NMR can provide insight into the molecular dynamics at the interface by probing the relaxation processes ($T_1$, $T_2$). This additional information can shed light on the interactions between the gas molecules and the hydrophilic or hydrophobic surface.

Experimental Systems

FIG. 1 is a schematic diagram of a system 100 for determining a wettability of a reservoir rock sample using the NMR gas isotherm technique. The system 100 includes NMR instrumentation, for example, a NMR control system 102 connected to a NMR magnet, for example, a first NMR magnet 104a or a second NMR magnet 104b or both. The NMR instrumentation can include either high or low field NMR instruments. The gas delivery system 120 includes a vapor expansion bulb, distribution chamber, pressure gauge, pump connection, and NMR sample cell. The NMR sample cell 122 is designed to sustain high pressure and high temperature (HPHT) conditions. For example, the NMR sample cell 122 can withstand up to 15,000 pounds per square inch (PSI) and up to 250 degrees Celsius (° C.) for substantially cylindrical samples of less than 5 millimeter (mm) diameter or up to 5,000 PSI and up to 150° C. for substantially cylindrical samples of about 1.5 inch diameter. The sample 112 can be any shape of porous media which will have size constraint by the dimension of NMR sample cell 122. The NMR control system 102 is configured to control the NMR instrumentation. For example, the NMR control system 102 can provide instructions to the NMR instrumentation to measure the total amount of protons inside the sample except the structural proton (part of solid). The system 100 can also include a computer system 108. The computer system 108 can construct the NMR gas isotherms using the total amount of gas (such as hydrocarbon gas or water vapor) adsorbed on the pore surfaces of porous reservoir rock sample. In some implementations, the computer system 108 can implement computer software operations to determine a wettability of the sample using techniques described later.

In some implementations, the sample 112 can be saturated with a liquid to a desired saturation level before being placed in the NMR sample cell 122. The liquid with which the sample 112 can be saturated can have a composition that is different from the gas provided by the gas delivery system 120. For example, the gas delivery system 120 can provide a hydrocarbon gas, and the sample 112 can be saturated with water. The water can include heavy water (also referred as deuterium oxide), such that the water that saturates the sample 112 is less likely to interfere with the NMR gas isotherms.

Each of the control system 102 and the computer system 108 can include one or more data processing apparatus (for example, one or more processors) and a computer-readable medium storing computer instructions executable by the data processing apparatus to perform operations including constructing NMR gas isotherms for samples and to determine wettabilities of the samples using the NMR gas isotherms. Each of the control system 102 and the computer system 108 can be implemented as a desktop computer, a laptop computer, a personal digital assistant (PDA), a smartphone, a tablet computer, or other computer. Alternatively, or in addition, each of the control system 102 and the computer system 108 can be implemented as firmware, software, or combinations of them. In some implementations, the control system 106 and the computer system 108 can be separate entities, while in some implementations, a single entity (for example, a single computer system) can include both the control system 102 and the computer system 108.

I. Experimental Conditions

A. NMR Gas Adsorption Isotherm Curve Construction

A reservoir rock sample can be placed inside the NMR sample cell included in the NMR instrumentation. The sample can include a rock core plug of any shape. For example, the rock core plug can be a cylindrical sample of substantially 1.5 inch diameter and 2 inch height. Alternatively, the sample can include rock chips (for example, drill cuttings). In other words, any shapes and sizes of porous media sample that fit into the NMR sample cell can be used.

The NMR experiments described here can be performed under laboratory conditions (for example, room temperature or pressure or both) or under reservoir conditions (for example, up to 150° C. and pressure up to 5000 PSI with the current commercially available technique for sample size of 1.5 inch diameter and 2 inches length cylindrical shape). The pressure in the NMR chamber is varied to construct the NMR gas isotherm curves. The initial pressure in the NMR sample cell can be set to any pressure, for example, atmospheric pressure or lower. For example, setting the initial pressure to the lowest possible pressure can enable a complete construction of the NMR gas isotherm curve, which can be beneficial for sub-micrometer sized pore systems. The techniques can be utilized in low field (for example, substantially 2 megahertz (MHz) to 20 MHz) or medium field (for example, substantially 20 MHz to 43 MHz) or high field (for example, substantially up to 900 MHz). The relaxation time distribution (T1 and T2) and Fast Fourier Transform (FFT) spectrum can be used to construct NMR gas adsorption isotherm curve for low and high field, respectively. The duration of the experiments can depend, in part, on the experimental setup, field strength, field homogeneity, other factors, or combinations of them.

To construct the NMR gas isotherm curve for the sample, the control system 106 can control the NMR instrumentation to measure the NMR gas isotherm starting with a dry sample and sequentially performing NMR measurement with while increasing the gas pressure within the NMR chamber. That is, the reservoir rock sample can be injected with gas (such as hydrocarbon gas or water vapor) under different pressures to detect adsorbed gas on the surface. In this manner, the reservoir rock sample can be wetted with an aqueous fluid at different pressures. The NMR instrumentation can detect the adsorbed gas signal and provide the detected information to the control system 102. Either the control system 106 or the computer system 108 (or both) can receive time domain raw data from the NMR instrumentation and invert the time domain raw data to relaxation time (T1 or T2) distribution for low field and FFT spectrum for high field NMR used as an input for the wettability calculation described later.

B. Wettability Measurement

Figure 2:
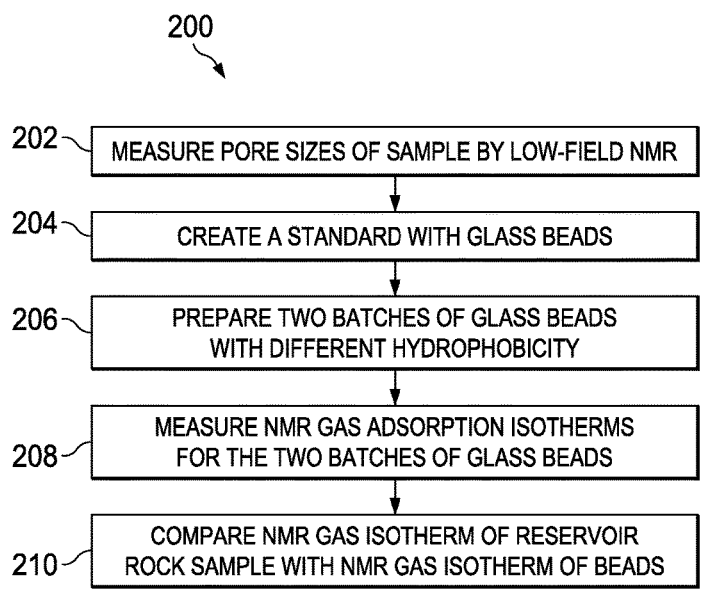
FIG. 2 is an example of a workflow for measuring wettability of a reservoir rock sample.

FIG. 2 is an example of a workflow 200 for measuring wettability of a reservoir rock sample. As described later, wettability of a reservoir rock sample can be quantified by comparing a NMR gas isotherm constructed for the reservoir rock sample with NMR gas isotherms constructed for hydrophilic and hydrophobic standards under similar conditions. At 202, pore sizes of the reservoir rock sample can be measured by low-field NMR. At 204, standards can be created to match the pore sizes of the reservoir rock sample. For example, beads (for example, glass beads, polymer beads, or beads made from other material) can be selected to create a pore system having substantially the same pore sizes as the reservoir rock sample. At 206, the standards can be separated into two batches and each batch can be coated with a hydrophilic coating and a hydrophobic coating, respectively. At 208, NMR gas isotherms can be constructed for the hydrophilic material coated standards and the hydrophobic material coated standards. At 210, the NMR gas isotherm of the reservoir rock sample can be compared with the NMR gas isotherms of the hydrophilic material coated standards and the hydrophobic material coated standards to quantify wettability.

II. Wettability Studies

Wetting is the ability of a liquid to maintain contact with a solid surface, which results from intermolecular interactions when two materials are brought together in contact. The wettability, which measures the degree of wetting, is the product of a force balance between adhesive and cohesive forces. Adhesion is the tendency of liquid molecules to create an attraction to a different substance. On the other hand, cohesion causes the liquid drop to create the minimum possible surface area. Hydrophobicity of a solid surface is caused by the adhesive force between liquid and solid. Therefore, wettability of the solid surface is directly related to hydrophobicity. Wettability studies are described in this disclosure in the context of reservoir rock samples, that is, rock samples that can be found in a hydrocarbon reservoir and that can trap hydrocarbons within their pore systems. The studies and the findings described in this disclosure can be applicable to any type of porous media, for example, porous media that include homogeneous pore systems (that is, having pores of substantially same size) or inhomogeneous pore systems (that is, having multiple pore sub-systems, each of different sizes).

The wettability studies can be implemented by applying a magnetic pulse sequence to a porous sample and measuring a NMR gas isotherm and a relaxation time of the pulse sequence. The magnetic pulse sequence applied to the sample can include a Carr-Purcell-Meiboom-Gill (CPMG) pulse sequence or a Spin-Echo Single Point Imaging (SE-SPI) pulse sequence. Implementing the CPMG pulse sequence can provide a global wettability index for a whole sample. Implementing the SE-SPI pulse sequence can provide multiple wettability indices for specific locations within the sample.

A. Wettability Studies Using CPMG Pulse Sequence

Figure 3:
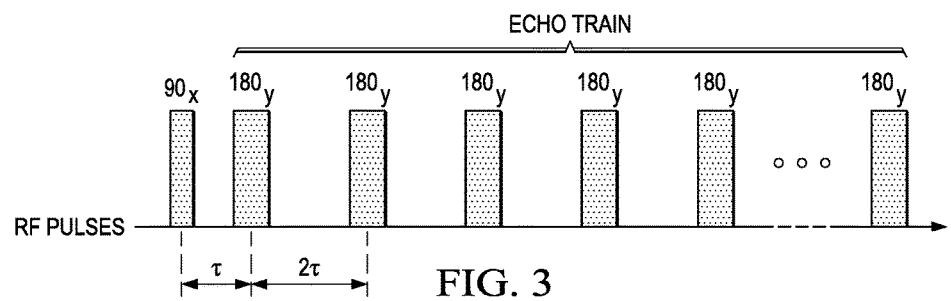
FIG. 3 is a schematic diagram of a Carr-Purcell-Meiboom-Gill (CPMG) pulse sequence.

FIG. 3 is a schematic diagram of a CPMG pulse sequence. The CPMG pulse sequence measures NMR T2 decay time. The T2 decay time measured using the CPMG pulse sequences can produce an averaged T2 distribution of the porous sample. A NMR gas isotherm can be constructed for the porous sample using techniques described earlier. In some implementations, a first pressure level is selected and an NMR gas isotherm is constructed for the porous sample at the selected first pressure level. The CPMG pulse sequence shown in FIG. 3 is applied to the porous sample to which the first pressure level is applied and the T2 decay time is measured. Subsequently, a second pressure level is selected and an NMR gas isotherm is constructed for the porous sample at the selected second pressure level. The CPMG pulse sequence shown in FIG. 3 is applied to the porous sample to which the second pressure level is applied and the T2 decay time is measured. The steps of constructing NMR gas isotherms and measuring T2 decay time in response to the CPMG pulse sequence are repeated for multiple pressure levels. A pressure-dependent T2 decay profile is created from the T2 decay times measured for the different pressure levels. The amount of gas adsorbed on the pore surface at each pressure can be calculated by measuring the total area changes of T2 distribution peak corresponding to the adsorbed gas which is created by inverting time domain T2 decay profile by CPMG experiment.

B. Wettability Studies Using Two-Dimensional SE-SPI Sequence

Figure 4A:
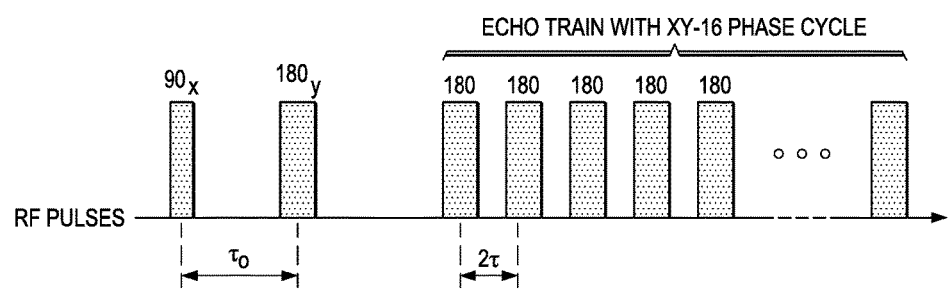
FIGS. 4A-4C are schematic diagrams of a Spin Echo Single Point Imaging (SE-SPI) pulse sequence.
Figure 4B:
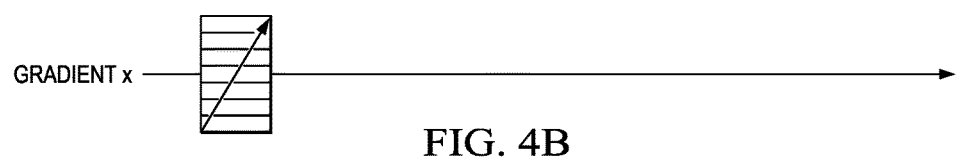
Figure 4C:

FIGS. 4A-4C are schematic diagrams of a SE-SPI pulse sequence. As described earlier, the NMR gas isotherm technique can be combined with T2 mapping techniques by SE-SPI pulse sequence to provide spatial wettability of the interior pore surface of any porous material including, for example, a sample of a reservoir rock. In such implementations, the SE-SPI pulse sequence can replace the CPMG pulse sequence that is used in wettability studies described earlier. The SE-SPI pulse sequence provides T2 distribution on a specific location within a sample by using a gradient-to-spatial encoding of the NMR signal. Thus, by combining the T2 mapping technique using the SE-SPI pulse sequence with the NMR gas isotherm method described earlier, spatial wettability distribution within a specific location (or specific locations) within a pore system can be measured.

In some implementations, a first pressure level is selected and an NMR gas isotherm is constructed for the porous sample at the selected first pressure level. The SE-SPI pulse sequence shown in FIGS. 4A-4C are applied to the porous sample to which the first pressure level is applied and the T2 decay time is measured. Subsequently, a second pressure level is selected and an NMR gas isotherm is constructed for the porous sample at the selected second pressure level. The SE-SPI pulse sequence shown in FIGS. 4A-4C is applied to the porous sample to which the second pressure level is applied and the T2 decay time is measured. The steps of constructing NMR gas isotherms and measuring T2 decay time in response to the SE-SPI pulse sequence are repeated for multiple pressure levels. A pressure-dependent T2 decay profile is created from the T2 decay times measured for the different pressure levels.

When applying the SE-SPI pulse sequence, the porous sample is divided into multiple slices, for example, along a longitudinal axis of the sample. For example, a porous sample that is about 2 inches thick can be divided into 64 slices. The pressure-dependent T2 decay profile is created from the T2 decay times measured for the different pressure levels in each slice. The amount of gas adsorbed on each slice of the pore surface at each pressure can be calculated by measuring the total area changes of T2 distribution peak corresponding to the adsorbed gas which is created by inverting time domain T2 decay profile by SE-SPI experiment. A wettability index can be determined for each slice using the techniques described later. Because each slice is taken at a specific location in the porous sample, wettability indices can be determined for multiple locations in the porous sample.

Figure 5:
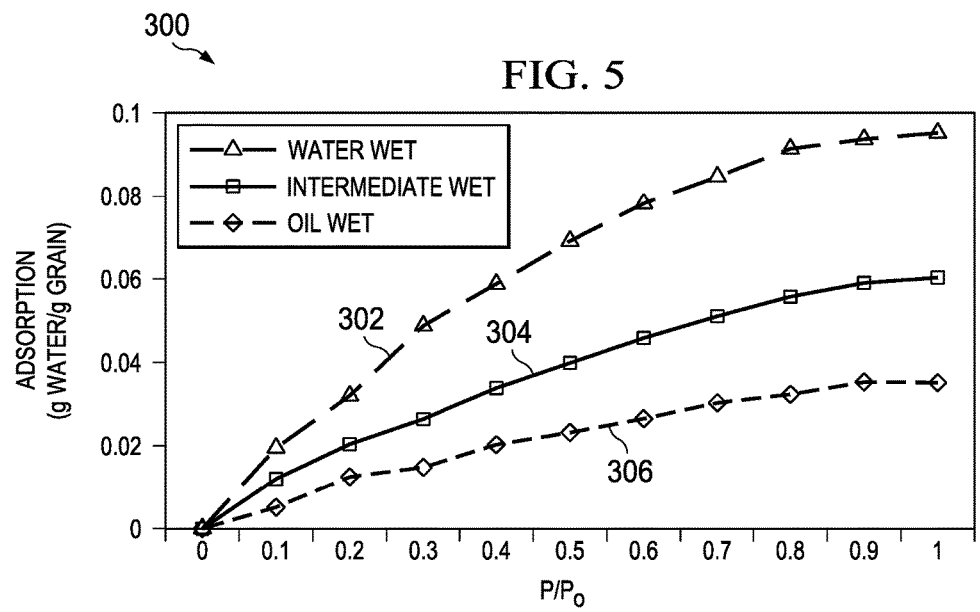
FIG. 5 is a schematic chart of relationships between NMR gas isotherms and surface wettability for reservoir rock samples.

FIG. 5 is a schematic chart of relationships between NMR gas isotherms and surface wettability for reservoir rock samples. The chart is a plot of adsorption (grams of gas divided by grams of grain) versus normalized pore pressure ($P/P_0$). The NMR gas isotherm curve is a gas adsorption isotherm curve, specifically, a hydrocarbon gas or water vapor adsorption isotherm curve. The detected hydrophobicity of the reservoir rock sample surface by NMR gas isotherm is a direct indication of native wettability of rock surface. That is, the surface with more hydrophilic nature will attract more water molecules to be adsorbed and resist hydrocarbon adsorption, whereas the surface with more hydrophobic nature will attract more hydrocarbon molecules to be adsorbed and resist water adsorption. FIG. 3 shows three NMR gas isotherm curves for three reservoir rock samples with different hydrophobicities. Hydrophobicity of reservoir rock can be divided into three categories—oil wet (that is, more affinity to hydrocarbons than water, and therefore, hydrophobic), water wet (that is, more affinity to water than hydrocarbons, and, therefore, hydrophilic) and intermediate wet (intermediate between oil wet and water wet). The line 302 represents the NMR gas adsorption isotherm for a water wet reservoir rock sample. The line 304 represents the NMR gas adsorption isotherm for an intermediate wet reservoir rock sample. The line 306 represents the NMR gas adsorption isotherm for an oil wet sample.

Figure 6:
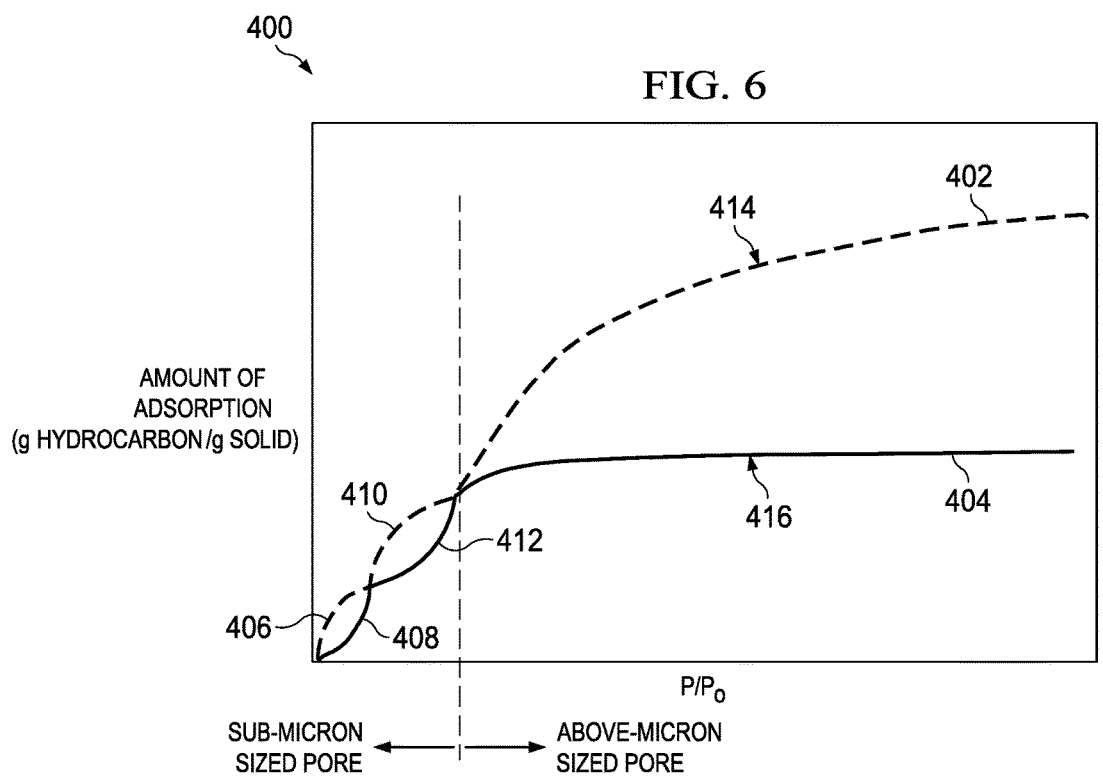
FIG. 6 is a schematic diagram of NMR gas isotherm of a porous reservoir rock sample that includes hydrophilic and hydrophobic surfaces.

FIG. 6 is a schematic diagram 400 of NMR gas isotherm of a porous reservoir rock sample that includes hydrophilic and hydrophobic surfaces. The reservoir rock sample can include multiple pore systems (for example, three pore systems as in FIG. 6), each with a different pore size. For example, some portions of the rock sample can include sub-micrometer sized pores, some portions of the rock sample can include pores greater than or equal to a micrometer in size, and some portions of the rock sample can include intermediate-sized pores between the sub-micrometer sized pores and the pores greater than or equal to a micrometer in size. In FIG. 6, the line 402 and the line 404 represent hydrophilic surfaces and hydrophobic surfaces, respectively, in such a reservoir rock sample with multiple pore systems. In such a rock sample, the NMR gas isotherm curve can be a combination of gas isotherm curves depending on the hydrophobicity of each pore system. For example, the hydrophobicity of the pore systems can be hydrophilic for the sub-micrometer sized pores (represented by line 406 in FIG. 6), hydrophobic for the intermediate-sized pores (represented by line 412 in FIG. 6) and hydrophilic for the pores greater than or equal to a micrometer in size (represented by line 414 in FIG. 6). In another example, the hydrophobicity of the pore systems can be hydrophobic for the sub-micrometer sized pores (represented by line 408 in FIG. 6), hydrophilic for the intermediate-sized pores (represented by line 410 in FIG. 6), and hydrophobic for the pores greater than or equal to a micrometer in size (represented by line 416 in FIG. 6). In other examples of mixed-sized pore systems with hydrophilic and hydrophobic surfaces, the NMR gas adsorption isotherm can include other combinations of the gas isotherm curves.

The dominant gas adsorption mechanisms for pores greater than or equal to a micrometer in size (diffusion) and sub-micrometer sized pores (capillary condensation) are different. For above-micrometer sized pore systems, hydrocarbon gas gets adsorbed on the hydrophobic surface (line 414 in FIG. 6) in greater amounts and faster as gas pressure is increased compared to hydrophilic surfaces (line 416 in FIG. 6). Thus, for pore systems with pores greater than or equal to a micrometer in size, the total amount of adsorbed gas can be used for the quantification of wettability, regardless of the isotherm curve shape.

For sub-micrometer sized pore systems, capillary condensation results in the same amount of gas being adsorbed on the pore surface regardless of hydrophobicity. Due to the differences in the adhesion force between gas and the surface for hydrophilic and hydrophobic cases, the shapes of NMR gas isotherm curves are also different. For example, hydrophilic and hydrophobic surfaces produce convex curve shapes (line 406, line 410 in FIG. 4) and concave curve shapes (line 408, line 412 in FIG. 4), respectively. Therefore, for sub-micrometer sized pore systems, curve shape analysis can be used for the quantification of wettability.

Figure 7:
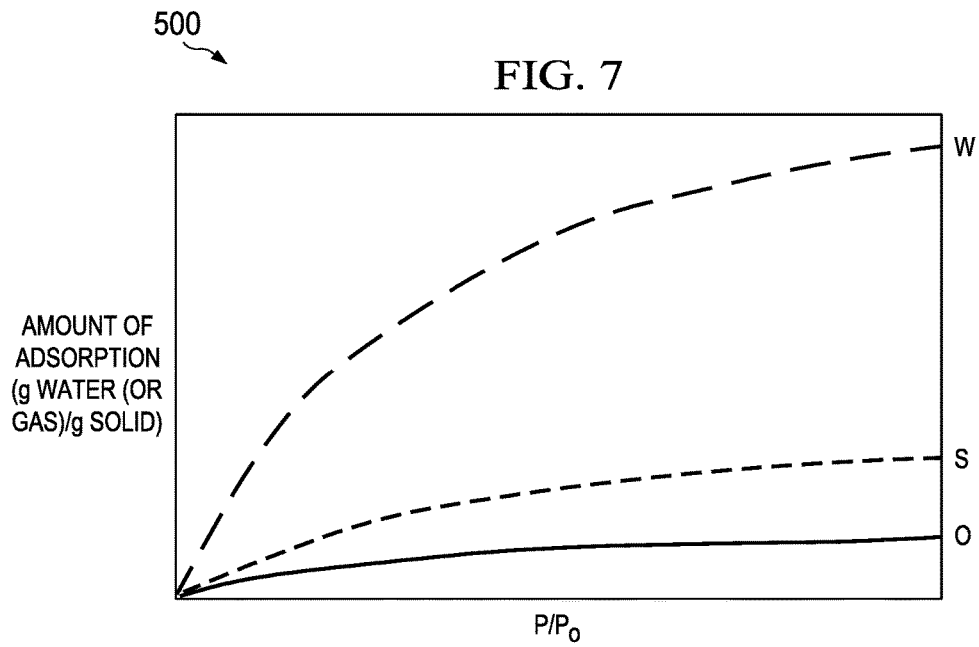
FIG. 7 is a schematic plot of sample NMR gas isotherm curves used to quantify wettability of a reservoir rock sample including pores greater than or equal to a micrometer in size.

FIG. 7 is a schematic plot 500 of sample NMR gas isotherm curves used to quantify wettability of a reservoir rock sample including pores greater than or equal to a micrometer in size. In some implementations, the wettability index of such a reservoir rock sample can be calculated using Equation 1:

$$WI_{pore\ size \geq micrometer} = \frac{S-O}{W-O}. \quad \text{(Equation 1)}$$

In Equation 1, $WI_{pore\ size \geq micrometer}$ is the wettability index by NMR gas isotherm for above-micrometer sized pore systems. Variables S, O and W represent the total amount of adsorption for sample, 100% oil wet standard and 100% water wet standard, respectively. For such pore systems, wettability can be quantified by:

$0.5 < WI_{pore\ size \geq micrometer} \leq 1$      Water wet:

$WI_{pore\ size \geq micrometer} \approx 0.5$      Intermediate wet:

$0 \leq WI_{pore\ size \geq micrometer} < 0.5$      Oil wet:

In some implementations, the NMR gas isotherm of standard coated with 100% hydrophobic material can be skipped by assuming the variable O in Equation 1 to be 0, resulting in Equation 2:

$$WI_{pore\ size \geq micrometer} = \frac{S}{W}. \quad \text{(Equation 2)}$$

Surface wetting is caused not only by pore surface chemistry but also by other physical factors, for example, surface roughness, pore structures, or other physical factors. Because Equation 2 does not account for such physical factors, a wettability measured using Equation 2, therefore, can be used as an approximation.

Figure 8:
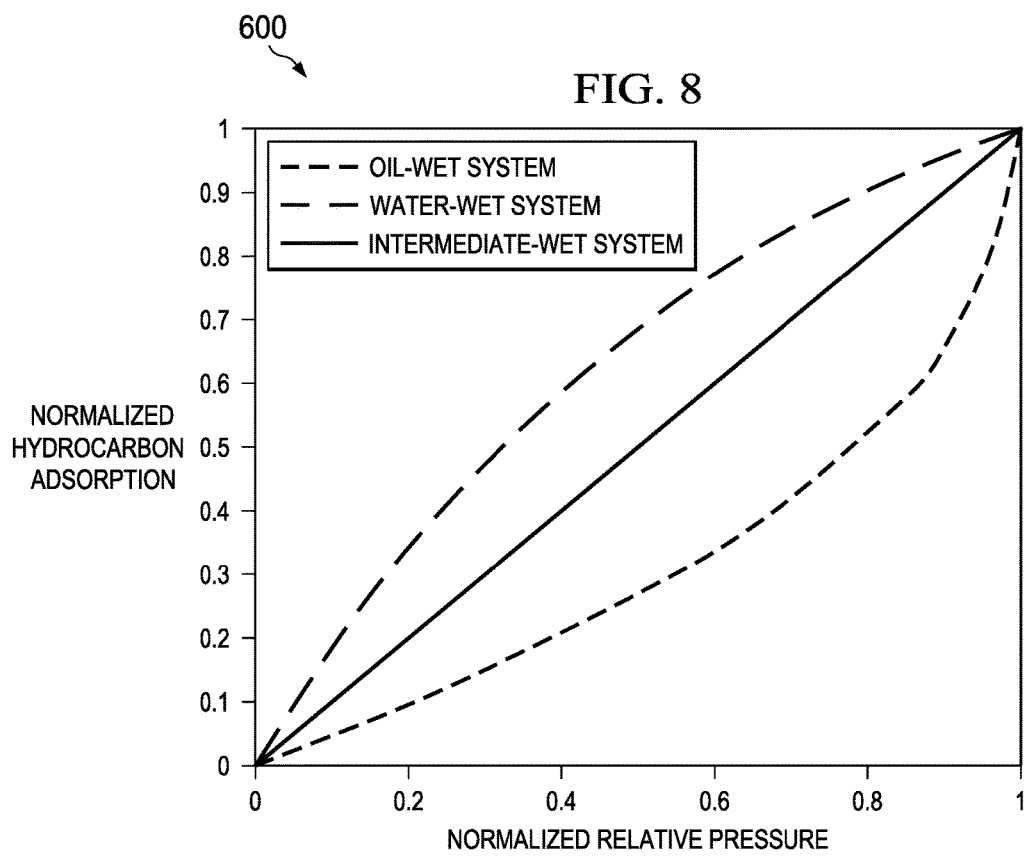
FIG. 8 is a schematic plot of sample NMR gas isotherm curves used to quantify wettability of a reservoir rock sample including sub-micrometer sized pores.

FIG. 8 is a schematic plot 600 of sample NMR gas isotherm curves used to quantify wettability of a reservoir rock sample including sub-micrometer sized pores. The plot 600 shows NMR gas isotherm curves for three sub-micrometer sized porous media with different wettabilities. For a water wet system the NMR gas adsorption curve is convex and for the oil wet system, the NMR gas adsorption curve is concave. In the case of intermediate-wet system the NMR gas adsorption curve lies between the convex and concave curves and is represented as a straight line in FIG. 6. As stated earlier, there is not much difference between the total amounts of adsorbed gas between the surfaces with different wettability for sub-micrometer sized pore systems. Consequently, wettability of a reservoir rock sample with sub-micrometer sized pores can be measured by the differences in curve shape rather than the end points, as was described earlier for a reservoir rock sample with pore systems with pores greater than or equal to a micrometer in size.

The non-uniform nature of the pore structures can result in the curvature of the NMR gas isotherm curves not being exactly convex, concave or straight. Therefore, the wettability can be determined by determining the area under the curve. To do so, in some implementations, the Trapezoidal rule can be implemented. Alternatively, other techniques to determine the area under the curve can also be implemented. Thus, in some implementations, the wettability index of a reservoir rock sample with sub-micrometer sized pores can be calculated using Equation 3 shown below.

$WI_{pore\ size < micrometer}$=Area under NMR gas isotherm curve.      (Equation 3)

Figure 9:
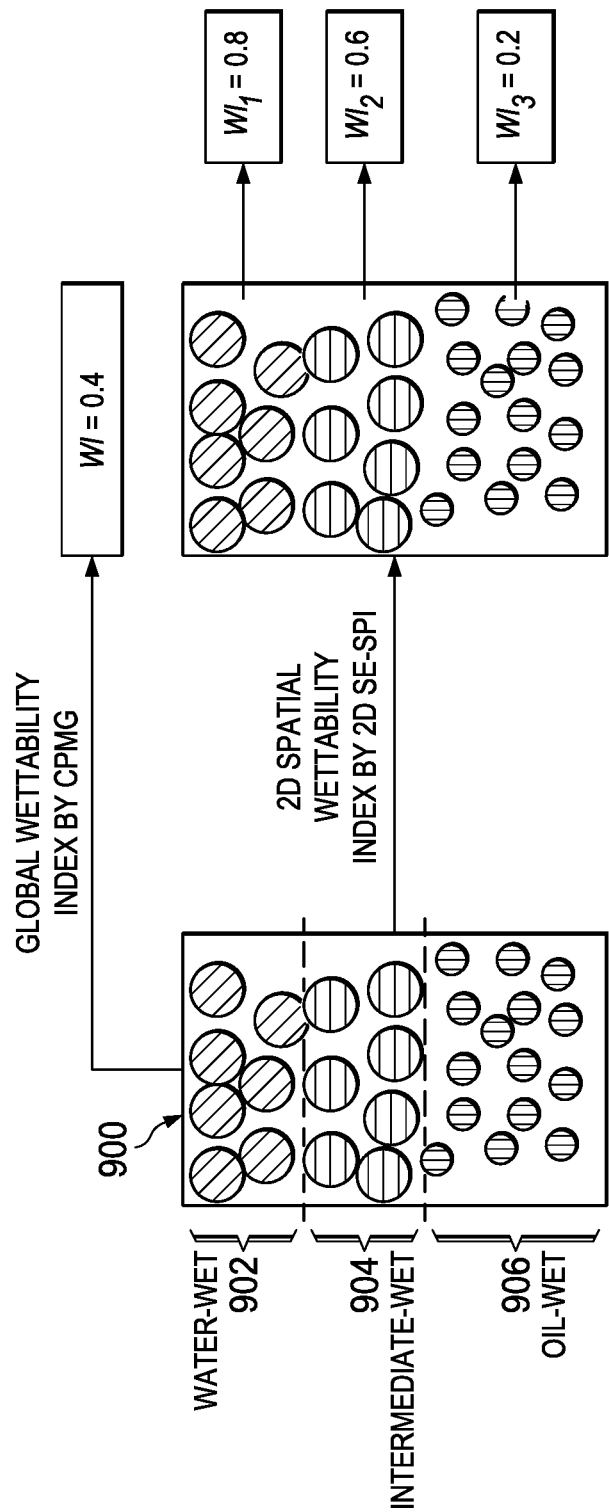
FIG. 9 is a schematic diagram showing example wettability indices measured from a NMR gas isotherm measured using the CPMG pulse sequence and a NMR gas isotherm measured using the SE-SPI pulse sequence.

For such pore systems, wettability can be quantified by:

$0.5 < WI_{pore\ size < micrometer} \leq 1$      Water wet:

$WI_{pore\ size < micrometer} \approx 0.5$      Intermediate wet:

$0 \leq WI_{pore\ size < micrometer} < 0.5$      Oil wet:

FIG. 9 is a schematic diagram showing example wettability indices measured from a NMR gas isotherm measured using the CPMG pulse sequence and a NMR gas isotherm measured using the SE-SPI pulse sequence. The schematic diagram shows a representation of a porous rock sample 900 that includes regions of different wettability. For example, the porous rock sample 900 includes a water-wet region 902, an oil wet region 906 and an intermediate wet region 904 having a wettability between those of the water-wet region 902 and the oil wet region 906. By implementing NMR gas isotherm measurement using a CPMG pulse sequence, a global wettability index of 0.4 is determined for the entire porous rock sample. By dividing the sample 900 into three regions and implementing NMR gas isotherm measurement using a SE-SPI pulse sequence in the three regions, three wettability indices of 0.8, 0.6 and 0.2 are determined for the water wet region 902, the intermediate wet region 904 and the oil wet region 906, respectively.

The wettability of the reservoir rock sample, determined by implementing the techniques described earlier, can be provided as an input variable to the computer system 108 that is executing a geophysical model of the hydrocarbon reservoir that includes reservoir rock substantially similar or identical to the reservoir rock sample. Using the input wettability, the computer system 100 can determine, model or simulate fluid flow through the hydrocarbon reservoir. By doing so, the computer system 100 can determine a total quantity of hydrocarbon reserve in the hydrocarbon reservoir or determine a production rate or both. In addition, the computer system 100 can use the wettability as an input parameter for models that measure, monitor, model or simulate enhanced oil recovery (EOR) or improved oil recovery (IOR) or both. In this manner, determining the wettability of a reservoir rock sample using the NMR gas adsorption isotherm technique described earlier can improve the accuracy of hydrocarbon reservoir simulation and help design more effective EOR/IOR techniques for the target hydrocarbon reservoir.

Figure 10:
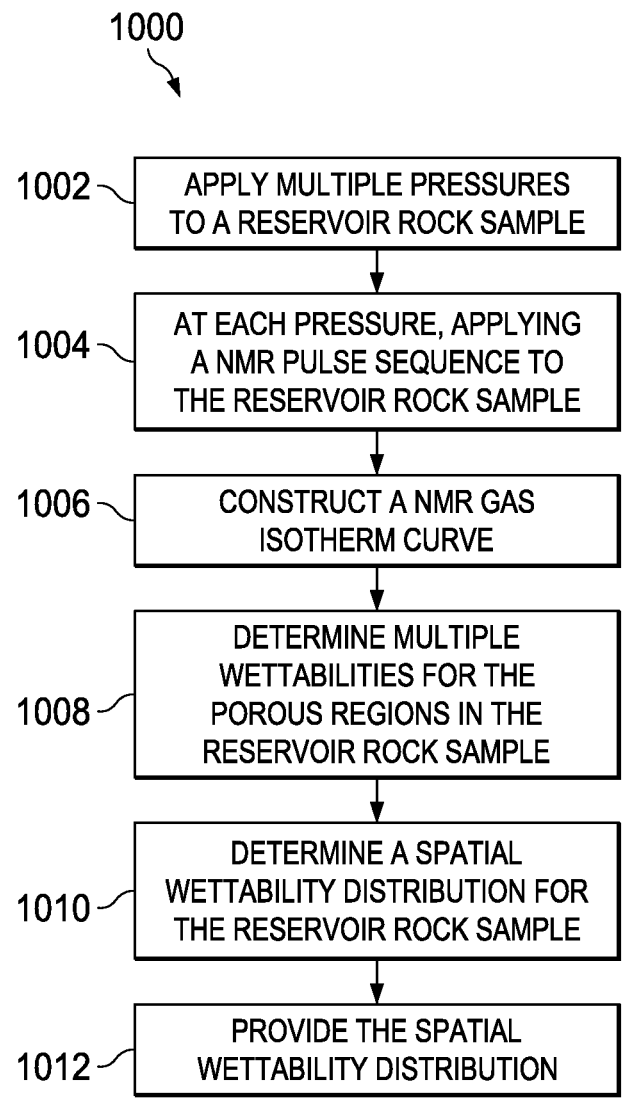
FIG. 10 is a flowchart of an example of a process for determining a spatial wettability distribution for a reservoir rock sample.

FIG. 10 is a flowchart of an example of a process 1000 for determining a spatial wettability distribution for a reservoir rock sample. At 1002, multiple pressures are applied to a three-dimensional reservoir rock sample in a closed volume. The reservoir rock sample includes multiple porous regions distributed along a longitudinal axis of the reservoir rock sample. The multiple porous regions have respective multiple wettabilities. Each wettability represents a quality of each porous region to absorb gas. At 1004 and at each pressure, a NMR pulse sequence is applied to the multiple porous regions distributed along the longitudinal axis of the reservoir rock sample. At 1006, a NMR gas isotherm curve is constructed for the reservoir rock sample in response to applying the multiple pressures and, at each pressure, applying the NMR pulse sequence to the multiple porous regions distributed along the longitudinal axis of the reservoir rock sample. At 1008, multiple wettabilities for the multiple porous regions are determined based on the NMR gas isotherm curve. Each wettability includes a value representing a quality of each porous region to absorb gas. At 1010, a spatial wettability distribution is determined for the reservoir rock sample based on the multiple wettabilities. At 1012, the spatial wettability distribution for the reservoir rock sample is provided. For example, the spatial wettability distribution can be displayed on a display device as shown in FIG. 9.

Thus, particular implementations of the subject matter have been described. Other implementations are within the scope of the following claims. For example, the techniques described above are in the context of NMR gas adsorption isotherms. To study the wettability of the reservoir rock sample using a hydrocarbon fluid, the appropriate hydrocarbon gas can be used instead of water vapor. Doing so can enable measuring the wettability for specific gas type in the inner surfaces of porous media.

The invention claimed is:

1. A method comprising:
    applying a plurality of pressures to a three-dimensional reservoir rock sample in a closed volume, the reservoir rock sample comprising a plurality of porous regions distributed along a longitudinal axis of the reservoir rock sample, wherein the plurality of porous regions have a respective plurality of wettabilities, each wettability representing a quality of each porous region to absorb gas;
    at each pressure of the plurality of pressures, applying a spin-echo single-point imaging (SE-SPI) pulse sequence to the plurality of porous regions distributed along the longitudinal axis of the reservoir rock sample;
    constructing a nuclear magnetic resonance (NMR) gas isotherm curve for the reservoir rock sample in response to applying the plurality of pressures and, at each pressure of the plurality of pressures, applying the SE-SPI pulse sequence to the plurality of porous regions distributed along the longitudinal axis of the reservoir rock sample;
    determining the plurality of wettabilities for the plurality of porous regions based on the NMR gas isotherm curve, each wettability of the plurality of wettabilities including a value representing the quality of each porous region to absorb gas;
    determining a spatial wettability distribution for the reservoir rock sample based on the plurality of wettabilities; and
    providing the spatial wettability distribution for the reservoir rock sample.

2. The method of claim 1, wherein the NMR gas isotherm curve comprises an NMR hydrocarbon gas adsorption isotherm curve, and the rock sample is saturated with water to a desired water saturation level.

3. The method of claim 1, further comprising:
    determining that the NMR gas isotherm curve is a convex curve; and
    determining that the reservoir rock sample comprises more hydrophilic surfaces than hydrophobic surfaces.

4. The method of claim 1, further comprising:
    determining that the NMR gas isotherm curve is a concave curve; and
    determining that the reservoir rock sample comprises more hydrophobic surfaces than hydrophilic surfaces.

5. The method of claim 1, wherein determining the spatial wettability of the reservoir rock sample comprises determining the spatial wettability based on whether the reservoir rock sample comprises more hydrophilic surfaces or more hydrophobic surfaces.

6. The method of claim 1, wherein a porosity of the plurality of porous regions ranges between less than a micrometer and greater than a micrometer, and wherein determining the spatial wettability of the rock sample comprises:
    determining a first wettability of a first porous region of the reservoir rock sample having a porosity less than a micrometer; and
    determining a second wettability of a second porous region of the reservoir rock sample having a porosity greater than or equal to a micrometer.

7. The method of claim 1, wherein determining the plurality of wettabilities for the plurality of porous regions based on the NMR gas isotherm curve, each wettability of the plurality of wettabilities including a value representing the quality of each porous region to absorb gas comprises: comparing the NMR gas isotherm curve for the reservoir rock sample with a first standard NMR gas isotherm curve for a hydrophobic sample and a second standard NMR gas isotherm curve for a hydrophilic sample.

8. The method of claim 7, further comprising:
    constructing a nuclear magnetic resonance (NMR) gas isotherm curve for the hydrophobic sample; and constructing a nuclear magnetic resonance (NMR) gas isotherm curve for the hydrophilic sample.

9. The method of claim 8, wherein the hydrophobic sample comprises beads coated with a hydrophobic coating, and wherein the hydrophilic sample comprises beads coated with a hydrophilic coating.

10. The method of claim 1, wherein determining the plurality of wettabilities for the plurality of porous regions based on the NMR gas isotherm curve, each wettability of the plurality of wettabilities including a value representing the quality of each porous region to absorb gas comprises:
determining a first quantitative value for a first porous region having a porosity ranging less than a micrometer; and
determining a second quantitative value for a second porous region having a porosity ranging greater than or equal to a micrometer.

11. The method of claim 10, wherein determining the first quantitative value comprises determining a normalized area under the NMR gas isotherm curve for the first porous region.

12. The method of claim 11, wherein determining the first quantitative value comprises determining that the reservoir rock sample is oil wet in response to determining that the normalized area under the curve is between 0 and substantially 0.5, determining that the reservoir rock sample is intermediate wet in response to determining that the normalized area under the curve is substantially equal to 0.5, or determining that the reservoir rock sample is water wet in response to determining that the normalized area under the curve is between substantially 0.5 and 1.

13. The method of claim 11, wherein determining the second quantitative value comprises determining a ratio of a difference between a hydrocarbon gas adsorption amount of the reservoir rock sample and a hydrocarbon gas adsorption amount of a hydrophobic sample and a difference between a hydrocarbon gas adsorption amount of a hydrophilic sample and the hydrocarbon gas adsorption amount of the hydrophobic sample.

14. The method of claim 13, wherein determining the second quantitative value comprises determining that the reservoir rock sample is oil wet in response to determining that the ratio is between 0 and substantially 0.5, determining that the reservoir rock sample is intermediate wet in response to determining that the ratio is substantially equal to 0.5, or determining that the reservoir rock sample is water wet in response to determining that the ratio is between substantially 0.5 and 1.

15. The method of claim 11, wherein determining the second quantitative value comprises determining a ratio between a hydrocarbon gas adsorption of the reservoir rock sample and a hydrocarbon gas adsorption of a hydrophilic sample.

16. The method of claim 1, wherein, at each pressure of the plurality of pressures, applying a SE-SPI pulse sequence to the plurality of porous regions distributed along the longitudinal axis of the reservoir rock sample comprises, while applying each pressure:
applying the SE-SPI pulse sequence to the plurality of porous regions in the reservoir rock sample; and
for each porous region, measuring a T2 decay time responsive to the applied pressure.

17. A system comprising:
a nuclear magnetic resonance (NMR) sample cell configured to receive a reservoir rock sample comprising a plurality of porous regions distributed along a longitudinal axis of the reservoir rock sample, wherein the plurality of porous regions have a respective plurality of wettabilities, each wettability representing a quality of each porous region to absorb gas;
a pressure delivery system connected to the NMR sample cell, the pressure delivery system configured to apply a plurality of pressures to the reservoir rock sample in the NMR sample cell;
a NMR control system connected to the NMR sample cell, the NMR control system configured to, at each pressure of the plurality of pressures, apply a spin-echo single-point imaging (SE-SPI) pulse sequence to the plurality of porous regions distributed along the longitudinal axis of the reservoir rock sample; and
a computer system connected to the NMR control system and the pressure delivery system, the computer system including a non-transitory computer-readable storage medium storing executable instructions to cause the computer system to perform operations comprising:
constructing a nuclear magnetic resonance (NMR) gas isotherm curve for the reservoir rock sample in response to applying the plurality of pressures and, at each pressure of the plurality of pressures, applying the SE-SPI pulse sequence to the plurality of porous regions distributed along the longitudinal axis of the reservoir rock sample;
determining the plurality of wettabilities for the plurality of porous regions based on the NMR gas isotherm curve, each wettability of the plurality of wettabilities including a value representing the quality of each porous region to absorb gas;
determining a spatial wettability distribution for the reservoir rock sample based on the plurality of wettabilities; and
providing the spatial wettability distribution for the reservoir rock sample.

18. The system of claim 17, wherein the pressure delivery system is configured to apply the plurality of pressures using hydrocarbon gas, the NMR gas isotherm curve comprises an NMR hydrocarbon gas adsorption isotherm curve, and the rock sample is saturated with water to a desired water saturation level.

19. The system of claim 17, wherein determining the plurality of wettabilities for the plurality of porous regions based on the NMR gas isotherm curve, each wettability of the plurality of wettabilities including a value representing the quality of each porous region to absorb gas comprises:
determining a first quantitative value for a first porous region having a porosity ranging less than a micrometer, wherein determining the first quantitative value comprises determining that the reservoir rock sample is oil wet in response to determining that the normalized area under the curve is between 0 and substantially 0.5, determining that the reservoir rock sample is intermediate wet in response to determining that the normalized area under the curve is substantially equal to 0.5, or determining that the reservoir rock sample is water wet in response to determining that the normalized area under the curve is between substantially 0.5 and 1.

20. The system of claim 17, wherein determining the plurality of wettabilities for the plurality of porous regions based on the NMR gas isotherm curve, each wettability of the plurality of wettabilities including a value representing the quality of each porous region to absorb gas comprises:
determining a second quantitative value for a second porous region having a porosity ranging greater than or equal to a micrometer, wherein determining that the reservoir rock sample is oil wet in response to determining that the ratio is between 0 and substantially 0.5, determining that the reservoir rock sample is intermediate wet in response to determining that the ratio is substantially equal to 0.5, or determining that the reservoir rock sample is water wet in response to determining that the ratio is between substantially 0.5 and 1.

\* \* \* \* \*